United States Patent [19]

Nogata et al.

[11] Patent Number: 5,728,461
[45] Date of Patent: Mar. 17, 1998

[54] FUNCTIONAL FIBER PRODUCTS AND PROCESS FOR PRODUCING THE SAME

[75] Inventors: Akihiro Nogata, Sabae; Hideyuki Yamada, Fukui; Masakazu Nomura, Takefu, all of Japan

[73] Assignee: Seiren Co., Ltd., Fukui-ken, Japan

[21] Appl. No.: 597,836

[22] Filed: Feb. 7, 1996

[30] Foreign Application Priority Data

Jul. 21, 1995 [JP] Japan .................................. 7-215101

[51] Int. Cl.$^6$ .................... D02G 3/00; D02D 3/00; B05D 3/04; B05D 3/02
[52] U.S. Cl. .................... 428/372; 428/375; 428/393; 428/394; 442/59; 442/97; 442/123; 442/125; 442/153; 442/154; 442/164; 442/165; 427/338; 427/385.5; 427/386; 427/389.9; 427/394
[58] Field of Search .................... 428/372, 375, 428/393, 394; 427/170, 393.1, 338, 372.2, 389.9, 392, 394, 396, 397, 385.5, 386; 442/59, 97, 123, 125, 153, 154, 164, 165

[56] References Cited

U.S. PATENT DOCUMENTS

Re. 35,151   1/1996   Hirukawa et al. .................. 428/393
5,047,266   9/1991   Mizushima et al. ................. 427/338

*Primary Examiner*—Patrick Ryan
*Assistant Examiner*—J. M. Gray
*Attorney, Agent, or Firm*—Dilworth & Barrese

[57] ABSTRACT

Functional fiber products are provided.

The functional fiber products are those adhered thereto a protein containing 20% to 40% by weight of serine as an amino acid component and those adhered thereto sericin and deacetylated chitin.

10 Claims, No Drawings

FUNCTIONAL FIBER PRODUCTS AND PROCESS FOR PRODUCING THE SAME

BACKGROUND OF THE INVENTION

The present invention relates to functional fiber products and a process for producing the same. Particularly, the present invention is concerned with a fiber product having a skin care property, an antibacterial fiber product, and a process for producing the same.

The "skin care property" as referred to herein indicates a property of protecting the skin and maintaining the skin in a moist state free of chapping.

The skin of a human body protects the body from various external environments while lying at the boundary between the body and the environments. It has been made clear by studies that the lipid and free amino acid surrounding the horny cells which form an epidermal horny layer of the skin plays a role of a natural moisture retaining factor.

Taking such a mechanism into account, various skin care cosmetics have heretofore been proposed and are in wide use for maintaining the skin in good condition and for preventing chapping of the skin, further for preventing surface exfoliation and deciduation of the horny layer caused by senescence of the skin.

Recently, attempts have been proposed to make the ordinary fiber products have the aforesaid functions required of cosmetics, and some clothes intended to attain the skin care effect during wearing have already been marketed. More particularly, it is known to use fibers consisting principally of protein or apply collagen to fiber procuts. However, problems are encountered in the characteristics of the fibers themselves or in the skin care property. A fiber product which exhibits a satisfactory skin care property while retaining satisfactory characteristics of the constitutent fibers is not known yet.

On the other hand, there have been known various fiber products having antibacterial property (including antimold property and deodorizing property).

In the cases of fiber products to be used in direct contact with the skin, for example, such clothes as underwear, undershirts, socks, shirts, blouses and lingeries, such bedclothes as sheets, quilt covers and pajamas, and such medical and sanitary materials as bandages, diapers and bed sheets, if secretions such as sweat and the like adhere to those fiber products, they serve as a source of nutrition, causing the growth of various bacteria and molds causing the emission of an offensive odor, or giving rise to a state which is not desirable from the hygienic viewpoint. In an effort to solve such problems there has been conducted a treatment for applying various synthetic antibacterial agents such as biguanide derivatives or organosilicon-based quaternary ammonium salts to fiber products such as fibers themselves or textile fabrics, or imparting an antibacterial property to them by ionic dissociation of antibacterial metals (Ag, Cu, Zn) suppported on zeolite.

In such fiber products obtained by those methods, however, the antibacterial agents used are not always safe to the human body, and in some particular use, they cause contact dermatitis to humans, especially those having a delicate skin such as newborn babies. Thus, safety problems have been encountered. As to some drugs, their use has been prohibited due to the occurrence of dioxin at the time of incineration. Thus, those antibacterial agents have been unsuitable as treating agents.

Recently, in reply to the demand for a safer antibacterial and deodorizing treatment or for providing a safer drug of a high molecular weight there have been proposed treating methods using as an antibacterial component a deacetylated chitin (hereinafter referred to as "chitosan") which is a natural substance (Japanese Patent Laid Open Nos. JP3-51369A, JP4-257301A, JP5-339801A and JP6-70803A). In these methods, however, chitosan is used as an antibacterial component, and for fixing it to fiber surfaces there is used a binder consisting principally of a synthetic resin which involves a problem in point of safety to the human body. Thus, even if the antibacterial effect and the washing durability in use of the treated fibrous materials are satisfied, no consideration is given to the human body, especially to the skin. This is the present situation and there has been a keen demand for improvement over these problems.

SUMMARY OF THE INVENTION

It is the first object of the present invention to provide a fiber product superior in the skin care property and capable of retaining the characteristics of the fiber material used, imparting a satisfactory moisture retaining effect to the horny layer and maintaining a moist skin over a long period.

It is the second object of the present invention to provide a fiber product superior in comfortableness and durability, highly safe to the human body, having excellent antibacterial, antimold and deodorizing properties and applicable to clothes at large, bedclothes, living-related materials and medical materials.

Further object of the present invention will become apparent from the following descriptions.

DETAILED DESCRIPTION OF THE INVENTION

The first object of the present invention is achieved by a fiber product having a skin care property and having a protein applied thereto which protein contains 20 to 40 wt % of serine as an amino acid component.

In the present invention, the use of a protein containing 20 to 40 wt % of serine as an amino acid component is advantageous in that when the textile product containing the said protein is in contact with the human skin, it maintains the horny layer of the skin highly hygroscopic to prevent the skin from becoming dry, thereby permitting the skin to be maintained in a moist state and preventing chapping and senescence of the skin. There are attained such outstanding effects.

Sericin is particularly preferred as the protein containing 20 to 40 wt % of serine. Sericin can be obtained by partial hydrolysis of sericin contained in silk fibers in accordance with a chemical scouring method or a fermentation scouring method, allowing it to be dissolved out and subsequently performing precipitation with a drug or any other suitable method to afford a sericin powder.

As examples of the fiber materials which constitute the fiber product according to the present invention there are mentioned raw fibers, yarns, piles, cotton-like matters, woven and nonwoven fabrics, knitted goods and woolplanted cloths. As examples of the fiber product are included not only the ordinary underwear and undershirts but also such clothes as supporters for hands and legs, socks, stockings and gloves. The fiber product as referred to herein further covers wood and paper products.

More particularly, any of, for example, synthetic fibers formed from thermoplastic polymers capable of forming fibers such as polyamides, polyesters, polyacrylonitriles and polyolefins, semisynthetic fibers such as acetate, as well as cellulosic fibers, animal, fibers, and mixtures of these fibers, may be used as constituent fibers of the fiber product. Particularly, it is desirable to use synthetic fibers as essential constituent fibers.

The amount of a predetermined protein, e. g. sericin, to be applied to the fiber product of the present invention is preferably in the range of 0.05 to 10 wt %, more preferably 0.2 to 3 wt %, based on the weight of the fibers used. If it is smaller than 0.05 wt %, it will be impossible to expect a moisture retaining effect, and even if it exceeds 3 wt %, no difference in effect will be recognized.

As the method for application of such protein there may be used a suitable means such as, for example, dipping, coating, spraying, or printing, using an aqueous solution of the protein.

It is possible to obtain the textile product in a dyed state, but in this case the protein applying operation should be performed after the dyeing operation.

In order to enhance the fixing of the protein in the invention there also may be used any of, for example, acrylic, urethane, polyester and epoxy resins.

It is preferable that an oil component, e. g. squalane, be used together with the protein containing 20 to 40 wt % of serine. Such a combined use permits ensuring of affinity, permeability and the supply of nutrition with respect to the skin and further permits preventing the emission of moisture from the skin to keep moderate the moisture and oil component in the skin.

The second object of the present invention is achieved by a fiber product wherein a composite of deacetylated chitin (chitosan) and sericin is fixed to the fiber surfaces.

The chitosan used in the present invention is one which exhibits antibacterial, antimold and deodorizing effects. A typical example thereof is an amino group-containing polymer (chitosan in a narrow sense) obtained through deacetylation of chitin by treatment with acid or enzyme and having a high molecular weight of several ten hundred thousand, the said chitin being obtained by removing such admixtures as calcium and proteins from the shells of the crustacean such as lobsters or crabs by treatment with acid and alkali. The chitosan in question may be a moderately decomposed polymer obtained by treating the said chitosan in a narrow sense with acid or enzyme and having a relatively low molecular weight of several thousand to several ten thousand. In view of the solubility in organic and inorganic acids and antibacterial property it is preferred that the degree of deacetylation of the chitosan be 50% or more.

As to antibacterial actions of chitosan there have been reported a mold growth inhibiting action and a growth inhibiting action against such Gram-positive and Gram-negative bacteria as *Escherichia coli, Staphylococcus aureus, Pseudomonas aeruginosa,* and *Bacillus subtilis*. Although the details of these antibacterial actions are uncertain, it is presumed that an anion constituent substance contained in the cell wall of bacteria is adsorbed by cationic amino groups of quaternized chitosan, resulting in biosynthesis of the cell walls being impeded or active transport of the substances present inside and outside the walls being inhibited, thus developing an antibacterial action.

Usually, chitosan and sericin are made into a mixed aqueous solution in the following manner, which solution is then applied to fibers. More specifically, sericin is first dissolved in water and then chitosan is dispersed in the resulting aqueous solution. Next, an inorganic acid or an organic acid is added under stirring to dissolve the chitosan, thereby preparing a mixed aqueous solution of chitosan and sericin.

Alternatively, an inorganic acid or an organic acid is added into an aqueous suspension of chitosan under stirring to prepare an aqueous chitosan solution and thereafter sericin is added to prepare a mixed aqueous solution of chitosan and sericin.

As an example of the inorganic acid is mentioned hydrochloric acid, while examples of the organic acid include acetic acid, lactic acid, formic acid, citric acid, succinic acid, gluconic acid, and ascorbic acid. Preferably the amount of the inorganic or organic acid used be not smaller than the amount necessary for neutralizing the free amino groups of chitosan and be adjusted so as to give a pH value of the resulting aqueous chitosan solution in the range of 3 to 6.

In the presence of sericin the swelling of film formed by chitosan alone is suppressed. Usually, both are used at a mixing ratio sufficient to suppress the water swelling of such chitosan film and to maintain the insolubilized state of the resulting film. A concrete mixing ratio differs depending on the molecular weight of chitosan, etc., but usually there is employed a mixing ratio at which the proportion of sericin is 0.01 to 2 times as large as the weight of chitosan and at which the above function is exhibited.

The concentration of chitosan and sericin in an aqueous solution is not specially limited and can be decided easily in accordance with a coating method to be used. In the case of a dipping method or the like, usually there is used a chitosan concentration of about 0.01 to 2 weight %.

The amount of chitosan and sericin to be fixed to the fiber surfaces is not specially limited if only the respective inherent functions are exhibited. Preferably, it is not smaller than 0.1 g/m$^2$, and from the standpoint of durability and hand the range of 0.2 to 5 g/m$^2$ is particularly preferred.

As mentioned above, it is optional whether the fibers to be applied with the above mixed aqueous solution is in the state of yarn or in the state of fabric. Also as to the method of application there may be adopted any of various known methods, including pad dry method, immersion method, and spray method.

The fibers thus applied with chitosan and sericin are dried and heated to fix a composite of the two onto the fiber surfaces. This drying and heating treatment is performed using a conventional hot air dryer or the like. As a temperature condition there is used a temperature range of 100° to 200° C. As to the conditions of apparatus and heating temperature and time, optimal conditions are determined in consideration of the production rate and while taking care so as not to exert a bad influence on the form and physical properties of the textile product after treatment.

According to the process of the present invention it is possible to obtain a fiber product having high safety and excellent hydrophilicity, antibacterial, antimold and deodorizing properties.

Particularly, in the case of using fibers essentially containing synthetic fibers such as polyester or nylon, it is possible to maintain the excellent physical properties inherent in the synthetic fibers, reduce a friction charging voltage which is a problem encountered in the synthetic fibers to an unsensitive degree to the human body, and develop antibacterial, antimold and deodorizing properties rich in durability and a lasting hydrophilic nature.

The fibers (fabric) thus treated may be combined with other suitable fibers (fabric).

In the process according to the present invention, the combination of chitosan and sericin is important and the presence of other components is not always necessary. But gelatin, synthetic peptides, and other components having a binder-like function, are also employable.

The present invention will be described below by way of working examples, but it is to be understood that the invention is not limited thereto.

[EXAMPLES]

Example 1

Tights obtained by weaving nylon yarn and Spandex yarn were immersed in a 3% aqueous sericin solution containing 25% of serine, then dehydrated using a centrifugal dryer and subsequently dried at 100° C. for 3 minutes to apply 0.8 wt % of sericin to the fibers.

The tights thus treated were put on by thirty women who had been chosen at random, and the women's skins were observed before and after wearing of the tights in accordance with the following evaluation conditions:

(1) Clothes: tights (nylon/Spandex)
(2) Wearing Period: 2 weeks (3) Evaluation:

①) In two weeks after wearing, the knee, shank and heel portions were observed for the state of skin in accordance with the following fives stages:
+2 . . . very moist
+1 . . . moist
0 . . . ordinary
−1 . . . chapping
−2 . . . heavy chapping ②) In two weeks after wearing and also in one month, the skin surfaces (shank and thigh portions) were observed through microscope photographs.

The results of evaluation are as shown in Table 1. At the beginning, among thirty panel members, chapping was recognized in fifteen members, of which twelve members (80%) were found to exhibit a chapping remedying effect after wearing.

From photographs of the skin surfaces there was observed exfoliation of horny layers before wearing, but after wearing it turned out that such exfoliation was remedied greatly.

TABLE 1

| Panelists | Site | State before Wearing | (Chapping) | State after Wearing | (Remedying Effect) |
|---|---|---|---|---|---|
| A | Knee | −1 | yes | 0 | yes |
|   | Shank | −1 |   | 0 |   |
|   | Heel | −1 |   | 0 |   |
| B | Knee | −2 | yes | 0 | yes |
|   | Shank | −1 |   | 0 |   |
|   | Heel | 0 |   | 0 |   |
| C | Knee | 0 | yes | 0 | yes |
|   | Shank | 0 |   | 0 |   |
|   | Heel | −2 |   | 1 |   |
| D | Knee | 0 | yes | 0 | yes |
|   | Shank | −1 |   | 0 |   |
|   | Heel | −1 |   | 0 |   |
| E | Knee | −1 | yes | 0 | no |
|   | Shank | 0 |   | 0 |   |
|   | Heel | −1 |   | −1 |   |
| F | Knee | −1 | yes | 2 | yes |
|   | Shank | −1 |   | 0 |   |
|   | Heel | −1 |   | 0 |   |
| G | Knee | −1 | yes | −1 | no |
|   | Shank | 0 |   | 0 |   |
|   | Heel | −1 |   | −1 |   |
| H | Knee | 0 | no | 0 |   |
|   | Shank | 0 |   | 0 |   |
|   | Heel | 0 |   | 0 |   |
| I | Knee | −2 | yes | −1 | no |
|   | Shank | −2 |   | −2 |   |
|   | Heel | −1 |   | −2 |   |
| J | Knee | 0 | yes | 0 | yes |
|   | Shank | −1 |   | 0 |   |
|   | Heel | −1 |   | 0 |   |
| K | Knee | 0 | yes | 0 | yes |
|   | Shank | −1 |   | 0 |   |
|   | Heel | −2 |   | 1 |   |
| L | Knee | 0 | no | 0 |   |
|   | Shank | 0 |   | −1 |   |
|   | Heel | 0 |   | 0 |   |
| M | Knee | 0 | no | 0 |   |
|   | Shank | 0 |   | 1 |   |
|   | Heel | 0 |   | 0 |   |
| N | Knee | 0 | no | 0 |   |
|   | Shank | 0 |   | 1 |   |
|   | Heel | 0 |   | 0 |   |
| O | Knee | 0 | yes | 1 | yes |
|   | Shank | −2 |   | 1 |   |
|   | Heel | 0 |   | 1 |   |
| P | Knee | 0 | no | 0 |   |
|   | Shank | 0 |   | 0 |   |
|   | Heel | 0 |   | 0 |   |
| Q | Knee | 0 | no | 0 |   |

TABLE 1-continued

| Panelists | Site | State before Wearing | (Chapping) | State after Wearing | (Remedying Effect) |
|---|---|---|---|---|---|
| | Shank | 0 | | 0 | |
| | Heel | 0 | | 0 | |
| R | Knee | −1 | yes | 1 | yes |
| | Shank | −1 | | 2 | |
| | Heel | −2 | | 1 | |
| S | Knee | 0 | no | 1 | |
| | Shank | 0 | | 0 | |
| | Heel | 0 | | 0 | |
| T | Knee | −1 | yes | 2 | yes |
| | Shank | 0 | | 2 | |
| | Heel | −1 | | 1 | |
| U | Knee | 1 | no | 1 | |
| | Shank | 1 | | 1 | |
| | Heel | 1 | | 1 | |
| V | Knee | 0 | no | 0 | |
| | Shank | 0 | | 0 | |
| | Heel | 0 | | 0 | |
| W | Knee | 0 | no | 0 | |
| | Shank | 0 | | 0 | |
| | Heel | 0 | | −1 | |
| X | Knee | 0 | no | 0 | |
| | Shank | 0 | | 0 | |
| | Heel | 0 | | 0 | |
| Y | Knee | −2 | yes | 1 | yes |
| | Shank | −1 | | 1 | |
| | Heel | 0 | | 1 | |
| Z | Knee | 1 | no | 1 | |
| | Shank | 0 | | 0 | |
| | Heel | 0 | | 0 | |
| a | Knee | 0 | no | 0 | yes |
| | Shank | 0 | | 1 | |
| | Heel | 0 | | 0 | |
| b | Knee | −2 | yes | 1 | |
| | Shank | −2 | | 1 | |
| | Heel | −1 | | 0 | |
| c | Knee | 0 | no | 0 | |
| | Shank | 0 | | 0 | |
| | Heel | 0 | | 0 | |
| d | Knee | 0 | no | 0 | |
| | Shank | 0 | | 0 | |
| | Heel | 0 | | 0 | |

Example 2

Swelling of Chitosan Film

At the proportions shown in Table 3 acetic acid was added to chitosan and dissolved by stirring to prepare aqueous chitosan solutions, then sericin was added as a fine powder and the same operation as above was repeated to afford aqueous mixed chitosan-sericin solutions of pH 4.

TABLE 3

| Drug | Recipe A | Recipe B | Recipe C |
|---|---|---|---|
| Chitosan | 0.5% | 0.5% | 0.5% |
| Sericin | 0.0% | 0.2% | 0.5% |
| Acetic Acid | 0.5% | 0.5% | 0.5% |

The aqueous solutions prepared above were each placed 10 ml in a Schale having an inside diameter of 85 mm and dried into film at 80° C. for 2 hours.

Then, a sample of 5.0 cm×2.0 cm was cut out of each film thus formed and immersed for 2 hours in distilled water held at 25° C., then measured for length to determine the degree of swelling in accordance with the following equation:

$$\text{Degree of swelling (\%)} = \frac{\text{Length after Immersion}}{\text{Length before Immersion}} \times 100$$

The degrees of swelling thus obtained are as set forth in Table 4.

TABLE 4

Degree of swelling of each film

| Recipe | Film Size after Immersion in distilled water (cm) | Degree of Swelling (%) |
|---|---|---|
| A | 7.8 | 156 |
| B | 5.3 | 106 |
| C | 5.1 | 102 |

The swelling degree of 100% means that the film concerned is not swollen at all.

The film from chitosan alone as in Table 3 has a degree of swelling as large as 156% and thus is presumed to be markedly deteriorated in strength. In contrast therewith, the films each containing 0.2% or 0.5% of sericin range from 102% to 106% in the degree of swelling and thus are little swollen, from which results those films are presumed to have no deterioration in strength. However, in the case where the amount of sericin was increased to twice or more as large as the amount of chitosan, the resulting film became difficult to be insolubilized and was dissolved when immersed in distilled water.

From the above results it turned out that the stability of chitosan film in water could be improved remarkably by adding sericin to chitosan.

Thus, by the addition of sericin to chitosan, the stability of chitosan film in water is greatly improved, and also when fixed to fibers, the durability thereof is improved to a great extent.

Example 3

Treatment of Fabrics with Chitosan/Sericin

Using the aqueous chitosan sericin solutions prepared in Example 1, three kinds of textile fabrics of polyester, nylon and cotton were treated under the following conditions:

1. Textile Fabrics

① Polyester fiber, Plain weave fabric
   Warp 75d/36f, Weft 75d/96f, Weight 80 g/m²
② Nylon fiber, Oxford
   Warp 70d/32f, Weft 165d/144f, Weight 100 g/m²
③ Cotton, Circular rib count 40
   Weight 150 g/m²

2. Treatment Conditions

The fabrics were immersed in the treating solutions and then squeezed with rubber rolls for application of 70% owf (based on the weight of the fabrics), thereafter heat-treated at 160° C. for 2 minutes.

3. Treated Fabrics

The relation between treated fabrics and the recipes in Example 2 is as shown in Table 3 below.

TABLE 5

| Recipe | Fabric |
| --- | --- |
| A | Fabric A |
| B | Fabric B |
| C | Fabric C |

The fabrics thus treated were then washed 10 times repeatedly and thereafter determined for antibacterial property, water absorption, moisture absorbing and releasing property, and friction charging voltage. The results obtained are as shown in Tables 6 to 8.

Washing Method:
   According to JIS L0217 103.

How to determine Antibacterial Property:
   Determined according to the Shaking Flask Method designated by the Textile Products Sanitary Processing Conference. The strain used in the determination was IFO13277.

How to determine Water Absorbing Property:
   According to JIS L1096A.

How to determine Moisture Absorbing and Releasing Property:
   In accordance with the official moisture content determining method defined by JIS L1096 the moisture content at 20° C., 65% RH and that at 40° C., 90% RH were measured and the difference between the two was calculated as the moisture absorbing and releasing property.

How to measure Frinction Charging Voltage:
   According to JIS L1094B.

TABLE 6

Results of the antibacterial property determination

| | Percent Sterilization (%) | | | |
| --- | --- | --- | --- | --- |
| Sample | Untreated | Treatment A | Treatment B | Treatment C |
| Polyester | 5 | 99 or more | 99 or more | 99 or more |
| Polyester Washing 10 times | 10 | 20 | 75 | 80 |
| Nylon | 10 | 99 or more | 99 or more | 99 or more |
| Nylon Washing 10 times | 12 | 19 | 68 | 76 |
| Cotton | 27 | 99 or more | 99 or more | 99 or more |
| Cotton Washing 10 times | 31 | 50 | 99 or more | 99 or more |

After the treatment, as is evident from Table 6, all of the polyester, nylon and cotton fabrics applied with chitosan exhibit a high antibacterial property. As to durability, however, in the case of treatment with chitosan alone (fabric A), the antibacterial property of the fabric after washing is greatly deteriorated after washing, whereas in the cases of fabrics B and C there is recognized little deterioration in antibacterial property even after washing ten times. Particularly in the case of polyester which is said difficult to ensure durability even with the use of a synthetic drug, there is attained a high durability.

TABLE 7

Results of the water absorbing property determination

| | Water Absorption Time (sec) | | | |
| --- | --- | --- | --- | --- |
| Sample | Untreated | A | B | C |
| Polyester | 180 or more | 33 | 4 | 3 |
| Polyester Washing 10 times | 180 or more | 180 or more | 2 | 2 |
| Nylon | 13 | 50 | 2 | 1 |
| Nylon Washing 10 times | 6 | 7 | 1 or less | 1 |
| Cotton | 5 | 30 | 1 or less | 1 or less |
| Cotton Washing 10 times | 3 | 8 | 1 or less | 1 or less |

As is evident from the results of the water absorbing property determination, in the cases of chitosan-sericin composites (recipes B and C) there were confirmed both high absorbing property and high durability. With chitosan alone, the water absorbing property is unsatisfactory, while in a composite form with sericin there is attained a high water absorbing property.

TABLE 8

Results of the moisture absorbing and releasing property determination

| Sample | Percent moisture absorption and release (%) Polyester |
| --- | --- |
| Untreated | 0.1 |
| Untreated Washing 10 times | 0.1 |
| A | 0.8 |
| A Washing 10 times | 0.1 |
| B | 1.2 |
| B Washing 10 times | 0.9 |
| C | 1.2 |
| C Washing 10 times | 1.0 |

As is evident also from the above table polyester exhibits no moisture absorbing and releasing property, while a high moisture absorbing and releasing property is attained by fixing chitosan or chitosan-sericin composite to fibers. Particularly with sericin added, a large value is obtained.

With chitosan or sericin alone, the durability attained is unsatisfactory, while in the form of a chitosan-sericin composite there is attained a high durability.

TABLE 9

Results of the friction charging voltage determination

| Sample | Friction Charging Voltage (V) | | | |
| --- | --- | --- | --- | --- |
|  | Untreated | A | B | C |
| Polyester | 6700 | 1300 | 1200 | 1200 |
| Polyester Washing 10 times | 4800 | 3200 | 1600 | 1500 |
| Nylon | 8000 | 6000 | 1500 | 1200 |
| Nylon Washing 10 times | 10000 | 8000 | 2500 | 1800 |
| Cotton | 850 | 500 | 300 | 450 |
| Cotton Washing 10 times | 500 | 550 | 250 | 300 |

A look at the above tables shows that the fabrics (recipes B and C) with chitosan-sericin composite fixed thereto are greatly decreased in friction charging voltage and are very high in durability.

What is claimed is:

1. A product comprising at least one fiber having a protein applied to a surface thereof, said protein containing 20% to 40% by weight of serine as an amino acid component.

2. A product as set forth in claim 1, wherein the protein is sericin.

3. A product as set forth in claim 1, wherein the protein is applied to the at least one fiber in an amount sufficient to impart a skin care property to the product.

4. A product as set forth in claim 1, wherein the protein is applied to the fiber in an amount of 0.05% to 10% by weight.

5. A product as set forth in claim 1, further comprising a binder resin selected from the group consisting of acrylics, urethanes, polyesters, epoxies, chitosan, gelatin and synthetic peptides.

6. A product comprising at least one fiber having sericin and deacetylated chitin applied to a surface thereof.

7. A product as set forth in claim 1 or claim 6, which is a woven or knitted fabric of vegetable fibers, regenerated fibers, semisynthetic fibers, or synthetic fibers.

8. A product as set forth in claim 1, wherein the protein is applied to the at least one fiber in an amount greater than 0.1 g/m$^2$.

9. A process comprising applying an aqueous solution of deacetylated chitin and sericin to the surface of at least one fiber, drying and heat-treating the at least one fiber.

10. A process as set forth in claim 9, wherein the at least one fiber is incorporated into a woven or knitted fabric.

* * * * *